(12) United States Patent
Fackelmeier

(10) Patent No.: US 10,708,551 B2
(45) Date of Patent: Jul. 7, 2020

(54) DATA TRANSMISSION UNIT AND IMAGING FACILITY WITH A CORRESPONDING DATA TRANSMISSION UNIT

(71) Applicant: Siemens Healthcare GmbH, Erlangen (DE)

(72) Inventor: Andreas Fackelmeier, Thalmaessing (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/224,983

(22) Filed: Dec. 19, 2018

(65) Prior Publication Data

US 2019/0199971 A1 Jun. 27, 2019

(30) Foreign Application Priority Data

Dec. 22, 2017 (EP) ..................................... 17210291

(51) Int. Cl.
| | |
|---|---|
| A61B 6/03 | (2006.01) |
| H04N 7/18 | (2006.01) |
| H04B 5/00 | (2006.01) |
| H01F 38/14 | (2006.01) |
| A61B 6/00 | (2006.01) |

(Continued)

(52) U.S. Cl.
CPC ............... *H04N 7/183* (2013.01); *A61B 6/56* (2013.01); *H01F 38/14* (2013.01); *H02J 50/10* (2016.02); *H04B 5/0025* (2013.01); *H04N 1/00095* (2013.01); *A61B 6/032* (2013.01); *A61B 6/035* (2013.01)

(58) Field of Classification Search
CPC ..... H04N 7/183; H04N 1/00095; H02J 50/10; A61B 6/56; A61B 6/032; A61B 6/035; H01F 38/14; H04B 5/0025
See application file for complete search history.

(56) References Cited

U.S. PATENT DOCUMENTS

| | | | |
|---|---|---|---|
| 5,787,212 | A | 7/1998 | Hong et al. |
| 2005/0040917 | A1 | 2/2005 | Schilling et al. |

(Continued)

FOREIGN PATENT DOCUMENTS

| | | |
|---|---|---|
| DE | 10206160 A1 | 8/2003 |
| DE | 102004031355 A1 | 10/2005 |

(Continued)

OTHER PUBLICATIONS

Yeh, C. et al. "The Essence of Dielectric Waveguides", California Advanced Studies, Los Angeles, USA, Springer US (2008), pp. 1-522, ISBN 978-0-387-30929-3.

(Continued)

*Primary Examiner* — Courtney D Thomas
(74) *Attorney, Agent, or Firm* — Harness, Dickey & Pierce, P.L.C.

(57) ABSTRACT

A data transmission unit includes a transmit unit and a receive unit. The transmit unit and the receive unit are relatively movable with respect to another of the receive unit and the transmit unit. The data transmission unit further includes a coupler, the receive unit being configured to receive data from the transmit unit via the coupler even during a relative movement between transmit unit and receive unit. The coupler includes a first dielectric waveguide including a conductor body and a retaining structure.

33 Claims, 3 Drawing Sheets

(51) Int. Cl.
*H02J 50/10* (2016.01)
*H04N 1/00* (2006.01)

(56) References Cited

U.S. PATENT DOCUMENTS

| | | | |
|---|---|---|---|
| 2007/0063785 A1* | 3/2007 | Krumme | A61B 6/56 |
| | | | 333/24 R |
| 2017/0105697 A1 | 4/2017 | Model | |
| 2017/0332991 A1 | 11/2017 | Fackelmeier et al. | |

FOREIGN PATENT DOCUMENTS

| | | |
|---|---|---|
| DE | 102013001667 A1 | 7/2014 |
| DE | 102014206295 A1 | 10/2015 |
| DE | 102015223068 A1 | 2/2017 |
| DE | 102016208539 A1 | 11/2017 |

OTHER PUBLICATIONS

European Search Report for European Application No. 17210291.5 Published Feb. 13, 2018.

* cited by examiner

DATA TRANSMISSION UNIT AND IMAGING FACILITY WITH A CORRESPONDING DATA TRANSMISSION UNIT

PRIORITY STATEMENT

The present application hereby claims priority under 35 U.S.C. § 119 to European patent application number EP 17210291.5 filed Dec. 22, 2017, the entire contents of which are hereby incorporated herein by reference.

FIELD

At least one embodiment of the invention generally relates to a data transmission unit, which has a transmit unit and also a receive unit able to be moved relative to the transmit unit and is configured for transmission of data from the transmit unit to the receive unit via a coupler even during a relative movement between transmit unit and receive unit, wherein the coupler has a first dielectric waveguide. Moreover at least one embodiment of the invention generally relates to an imaging facility with a corresponding data transmission unit.

BACKGROUND

A computed tomograph typically has a fixed base and what is referred to as a gantry, wherein the gantry, during operation, i.e. during an acquisition of data via an x-ray detector, moves relative to the fixed base and, in doing so, performs a rotational movement. In this case the x-ray detector, with the aid of which the generation of data is undertaken for creating an image, is usually part of the gantry, so that the data generated in operation has to be transmitted from the gantry via a data transmission path back to the fixed base and usually through to a processing unit for the generated data.

The generated data is typically transmitted via the data transmission path in such cases, without any intermediate storage or relevant buffering and accordingly effectively in parallel to the generation of corresponding data and i.e. thus also during the rotation of the gantry. Data transmission paths suitable for this are known in principle from the prior art, wherein in most cases, what is known as a slip ring is part of a corresponding data transmission path.

An alternate embodiment of a data transmission path suitable for such a data transmission is described in DE 10 2016 208 539 A1, the entire contents of which is hereby incorporated herein by reference. This comprises a dielectric waveguide and is also suitable for non-contact data transmission.

SUMMARY

At least one embodiment of the invention specifies an advantageous solution for data transmission.

Embodiments of the invention are directed to a data transmission unit and also an imaging facility. Preferred developments are contained in the claims. The advantages and preferred embodiments stated in respect of the data transmission unit are also able to be transferred analogously to the imaging facility and vice versa.

At least one embodiment of the invention relates to a data transmission unit, having a transmit unit and a receive unit, which are able to be moved relative to one another, and configured for transmission, especially for non-contact transmission, of data from the transmit unit to the receive unit via a coupler, and expediently for doing so even during a relative movement between the transmit unit and the receive unit. Here the coupler also has a first dielectric waveguide, wherein the first dielectric waveguide has a conductor body and a retaining structure.

In an embodiment, the conductor body can be embodied in particular for conveying electromagnetic waves from the frequency range of 40 to 300 GHz.

At least one embodiment of the invention relates to an imaging facility including a data transmission unit of an embodiment.

BRIEF DESCRIPTION OF THE DRAWINGS

Example embodiments of the invention will be explained in greater detail below with reference to a schematic drawing. In the figures.

Parts corresponding to one another are provided with the same reference characters in all figures in each case.

DETAILED DESCRIPTION OF THE EXAMPLE EMBODIMENTS

Figure 1:
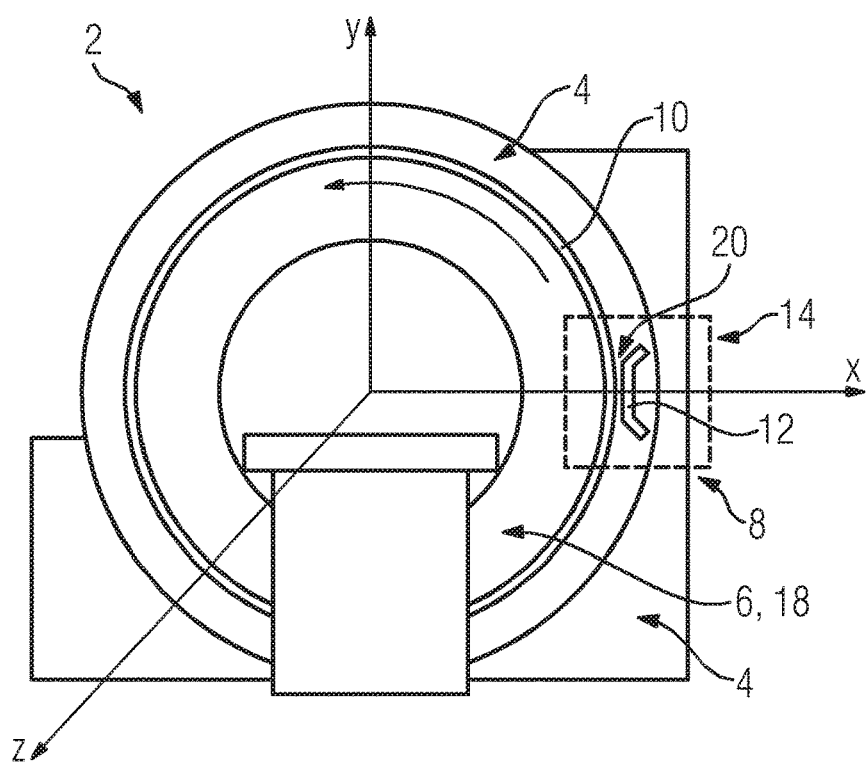
FIG. 1 shows, in a kind of cross-sectional diagram, a computed tomograph with a groove and a first dielectric waveguide inserted into the groove.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCam1, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention relates to a data transmission unit, having a transmit unit and a receive unit, which are able to be moved relative to one another, and configured for transmission, especially for non-contact transmission, of data from the transmit unit to the receive unit via a coupler, and expediently for doing so even during a relative movement between the transmit unit and the receive unit. Here the coupler also has a first dielectric waveguide, wherein the first dielectric waveguide has a conductor body and a retaining structure. The conductor body can be embodied in particular for conveying electromagnetic waves from the frequency range of 40 to 300 GHz.

The transmit unit and the receive unit are then able to be moved relative to one another in particular when the receive unit is able to be moved relative to the transmit unit. The transmit unit and the receive unit are then able to be moved relative to one another in particular when the transmit unit is able to be moved relative to the receive unit.

In particular a data transmission unit is disclosed with at least one embodiment of the invention that has a transmit unit and also a receive unit able to be moved relative to the transmit unit and configured for transmission of data from the transmit unit to the receive unit via a coupler even during a relative movement between transmit unit and receive unit, wherein the coupler has a first dielectric waveguide, wherein the first dielectric waveguide has a conductor body and a retaining structure.

The retaining structure can be embodied in particular for fixing, for example for detachable fixing, of the first dielectric waveguide to a module or unit. The retaining structure can be embodied in particular for fixing, for example for detachable fixing, of the first dielectric waveguide to a gantry support structure of a computed tomograph.

The gantry support structure of the computed tomograph can be a gantry support structure of a rotatable gantry of the computed tomograph for example. In particular the gantry support structure can feature the module and/or the unit.

In this case the conductor body primarily serves to convey electromagnetic waves, while the retaining structure is used primarily to fix the first dielectric waveguide and in particular the conductor body to a module or unit provided for this purpose and thus to hold the conductor body on the corresponding module or unit. This means that the first dielectric waveguide is preferably embodied and/or fixed to a module or unit intended for this purpose such that the electromagnetic field, when electromagnetic waves are being conveyed through the first dielectric waveguide, essentially only extends out over the volume of the conductor body and in particular only extends to a small degree into the volume of the retaining structure.

The first dielectric waveguide is further usually supplemented by a second dielectric waveguide, wherein the first dielectric waveguide is typically part of the transmit unit and the second dielectric waveguide is expediently part of the receive unit. During operation of the data transmission unit there is then usually a data transmission, in particular a non-contact data transmission, from the first dielectric waveguide to the second dielectric waveguide, via an air gap separating the two dielectric waveguides for example and accordingly the two dielectric waveguides are typically also part of the coupler.

A corresponding data transmission via dielectric waveguides is expediently undertaken in this case according to a principle known per se. Depending on embodiment variant, the data transmission unit is embodied in this case as a monodirectional or as a bidirectional data transmission unit, wherein especially in the latter case, a number of couplers of the type stated previously are preferably realized and wherein each coupler then has at least two dielectric waveguides.

A data transmission unit of this type is preferably embodied in this case for an imaging facility, such as for example a computed tomograph or a magnetic resonance tomograph, and accordingly preferably realized in or built into its imaging facility. This means that a data transmission unit presented here and in particular a first dielectric waveguide described in greater detail below is used in an imaging facility, as is described in particular in DE 10 2016 208 539 A1 or in DE 10 2015 223 068 A1, the entire contents of each which are hereby incorporated herein by reference. In at least one embodiment of this invention the data transmission unit described here then replaces the data transmission units or transmission paths described in these publications in each case and in particular a dielectric waveguide or the dielectric waveguides described therein are replaced by the first dielectric waveguide described in greater detail below. Explicit reference is thus made at this point to the descriptions in the two publications.

Preferred here is a version of the data transmission unit and in particular of the first dielectric waveguide and/or of the second dielectric waveguide, in which the conductor body of the first dielectric waveguide and/or the conductor body of the second dielectric waveguide forms a kind of profile strip or a kind of profile strand and in particular has an end-to-end uniform cross-section here.

The corresponding cross-section is embodied round or square-shaped for example in this case and the profile strip or the strand profile expediently forms a strand profile extended in a longitudinal direction or a profile strip extended in a longitudinal direction. At least in the installed state, the profile strip or the strand profile further preferably forms a type of ring body, which is arranged for example running around the circumference of a cylindrical body. If the data transmission unit is then part of a computed tomograph with a cylindrical gantry for example, then the dielectric waveguide, in accordance with one embodiment variant, runs on the circumferential side around the gantry, in a similar way to a slip ring in computed tomographs with such a device.

It is further of advantage for the conductor body and the retaining structure and in particular the entire first dielectric waveguide to be made of the same material. In such a case the first dielectric waveguide is then in particular embodied in one piece, in one section and thus effectively monolithically. The same preferably applies also or as an alternative to the second dielectric waveguide.

According to an alternate embodiment the retaining structure of the first dielectric waveguide and/or the retaining structure of the second dielectric waveguide is embodied in the manner of a separate structure, wherein in this case the retaining structure and the conductor body typically are made of of different materials. Here the conductor body is then embedded in the retaining structure for example and in this way will then be held by the retaining structure, which for its part is fixed or anchored to a module or unit. In accordance with one embodiment variant the retaining structure is then embodied in the manner of a part shroud or a part foam enclosure, in which the conductor body, seen in cross-section, is free, at least in a circumferential area, i.e. effectively on one side and in the other circumferential areas is surrounded by the retaining structure.

If the conductor body and the retaining structure are realized from different materials, then the retaining structure preferably includes of a (micro)porous or foam-type material. Also useful here is a material for the retaining structure of which the dielectricity value, permittivity value or relative permittivity has an approximate value of 1, i.e. lies in the range 1 to 1.5 for example.

The conductor body is furthermore made of Teflon or a polyethylene and is expediently designed for conveying electromagnetic waves for the frequency range 40 to 300 GHz, i.e. for example around 60 GHz. The same also applies to the conductor body, provided the conductor body and the retaining structure are made of the same material, and over and above this preferably to the entire first dielectric waveguide and/or the entire second dielectric waveguide, provided this is made or these are made from a single material, i.e. are effectively designed monolithically.

In particular, when the conductor body and the retaining structure and especially the entire first dielectric waveguide are made of the same material, the retaining structure further preferably forms the first part of a plug connection, i.e. of a mechanical plug connection, so that the first dielectric waveguide can be attached for example simply by plugging-in or clipping-in. This means that the first dielectric waveguide, the principle in this case also being transferrable to the second dielectric waveguide, is preferably fixed as part of the realization of the data transmission unit and in particular in the course of the manufacturing of an imaging facility with the aid of the retaining structure and by embodying a plug connection on a module or unit and is thus attached detachably to the corresponding module or unit. Accordingly the unit or module then has the second part of the plug connection, which is embodied for example by a number of recesses or grooves.

In an advantageous development the second part of the plug connection is embodied in the manner of a receptacle with an undercut. If the plug connection is then made and the retaining structure or the first electrical waveguide is lying in the receptacle, then the retaining structure or the first dielectric waveguide effectively grips behind the undercut. This means that the plug connection is preferably embodied such that the retaining structure or the first dielectric waveguide, when the plug connection is made, will not be held or will not only be held by a force fit but also by a form fit. To make it easier to establish the plug connection, the retaining structure or the first dielectric waveguide is then further preferably embodied at least partly elastically.

According to one embodiment variant, the retaining structure further has a number of retaining arms or is embodied by a number of retaining arms, which are formed on the conductor body and typically extend in the plug-in direction of the plug connection. In this embodiment the retaining arms are preferably arranged evenly, i.e. in particular in the manner of an even distribution, distributed over the longitudinal extent and in particular over the extent in the longitudinal direction of the first dielectric waveguide.

As an alternative or in addition hereto, the first dielectric waveguide forms a kind of profile strip or strand profile, which further preferably has an end-to-end uniform cross-section. In this case the plug connection is then designed similar to a tongue-in-groove joint or similar to a tongue-and-groove joint or similar to a dovetail joint. That connection extends in accordance with an embodiment variant in this case preferably over at least 50% of the longitudinal extent, further preferably over at least 75% and in particular essentially along the entire longitudinal extent of the first dielectric waveguide.

The profile strip embodying the first dielectric waveguide, seen in cross-section, further has a number of retaining webs, which extend transversely to the longitudinal extent, i.e. typically transversely to the extent in the longitudinal direction and moreover also preferably transversely to the plug-in direction of the plug connection, i.e. to the direction in which the first dielectric waveguide is to be routed, in order to establish the plug connection. These retaining webs, according to a further preferred embodiment variant, form the retaining structure and, when the plug connection is made for example, engage behind an undercut, so that then the plug connection is not embodied or is not only embodied as a force-fit connection but also as a form-fit connection.

In an advantageous development, seen in cross-section, a retaining web is formed onto the conductor body, on two opposing sides of the conductor body, in each case, and is formed directly onto the conductor body without a further intermediate geometrical shape. The first dielectric waveguide, seen in cross-section, then typically exhibits a shape with a square-shaped belly, the conductor body, to which two wings lying opposite one another, the two retaining webs, are connected.

In this case the shape of the retaining webs, the shape of the conductor body and the relative position at which the retaining webs are formed on the conductor body varies, depending on embodiment variant and application purpose. Thus the retaining webs, in accordance with one embodiment variant, seen in cross-section, taper towards the outside, i.e. in a direction transverse to the longitudinal direction and transverse to the plug-in direction of the plug connection as well as directed away or pointing away from the conductor body.

As an alternative or in addition hereto, the retaining webs, seen in cross-section, are angled, and are indeed angled in particular against the plug-in direction of the plug connection. In this case the retaining webs, when the plug connection is made, then grip behind an undercut as a kind of barb.

Also useful is a version in which the retaining webs, seen in cross-section, make a flush joint with an upper side of the conductor body, usually on an upper side, of which the normal is directed against the plug-in direction of the plug connection. In such a version the first dielectric waveguide, seen in cross-section, then typically has a kind of T shape.

Further preferred is that the contact between the first dielectric waveguide and the unit or module that features the second part of the plug connection, is restricted to a minimum, and that this is done in particular in the area of the outer ends of the retaining webs. In all other areas there is preferably a free space around the first dielectric waveguide, in which typically air is present. This has a favorable effect on the attenuation characteristics of the first dielectric waveguide.

As already mentioned previously, a data transmission unit presented here is embodied for an imaging facility and accordingly a data transmission unit presented here will preferably be used in an imaging facility. An embodiment of an inventive imaging facility is then preferably embodied as a computed tomograph or magnetic resonance tomograph and has a data transmission unit according to one of the embodiment variants given above.

According to a preferred embodiment variant, the imaging facility is embodied in this case as a computed tomograph and has a fixed base as well as a rotatable gantry with a gantry support structure. In this case the transmit unit is then preferably part of the rotatable gantry and the first dielectric waveguide, which usually also embodies the transmit unit, is preferably fixed to the gantry support structure. Here the first dielectric waveguide is preferably fixed to the gantry support structure with the aid of a plug connection, in particular a plug connection of the type previously described and in this case the gantry support structure preferably has a groove, which forms a part of the plug connection, in particular the second part for a previously described first part, i.e. a first part embodied by the first dielectric waveguide.

A corresponding groove is further preferably embodied in this case as a circumferential groove, which runs around the circumference of the gantry. Moreover it is advantageous when the first dielectric waveguide is arranged recessed into the groove after the plug connection has been made.

An imaging facility described by way of example below and outlined in FIG. 1 is embodied as a computed tomograph 2 and has a fixed base 4 as well as a rotatable gantry 6. Here the gantry 6 is embodied according to the known principle for generation of image data via an x-ray detector not shown and accordingly data is then generated during operation of the computed tomograph 2, which is to be transmitted during the rotation of the gantry 6 from the rotatable gantry 6 to the fixed base 4 and is transmitted via a data transmission unit 8.

A first dielectric waveguide 10 and also a second dielectric waveguide 12 are part of this data transmission unit 8, in one embodiment, which can be preferrably, in an embodiment, arranged in relation to one another such that there is an air gap 20 of on average around 1 mm between the two, which during rotation of the gantry 6 varies over a range of 0.5 mm and 1.5 mm. According to a known principle image data is able to be transmitted across this air gap 20 from the first dielectric waveguide 10 to the second dielectric waveguide 12 and thus from the rotatable gantry 6 to the fixed base 4. The first dielectric waveguide 10 is thus part of a transmit unit, while the second dielectric waveguide 12 is part of a receive unit. Moreover the first dielectric waveguide 10 and the second dielectric waveguide 12 also form a coupler 14, which couples the base 4 and the gantry 6 for signaling purposes.

In a preferred embodiment the first dielectric waveguide 10 is designed in the shape of a ring in this case or assumes a ring-shaped design in its installed state, as is indicated in FIG. 1. Thus, in its installed state, the first dielectric waveguide 10 runs around the circumference of the rotatable gantry 6 and is preferably arranged in this case recessed in a groove 16. That groove 16 is part of a gantry support structure 18 here and preferably forms a second part of a plug connection, via which the first dielectric waveguide 10 is attached to the gantry support structure 18.

The first part of the plug connection supplementing the second part of the plug connection embodies the first dielectric waveguide 10, which is preferably embodied in the manner of a profile strip or strand profile in the example embodiment. That profile strip or that strand profile preferably has a uniform cross-section in this case extending over the entire longitudinal extent of the first dielectric waveguide 10.

The corresponding profile strip or the corresponding strand profile is further preferably embodied in one piece, in one section and effectively monolithically and is made of Teflon or polyethylene for example.

The shape of the first dielectric waveguide 10 is preferably able to be subdivided into different areas in this case, which differ according to their function. Thus the first dielectric waveguide 10 expediently has a conductor body 22, which is embodied in a square shape for example and which is usually adjoined by a retaining structure 24. In this case the conductor body 22 primarily serves to convey electromagnetic waves and the retaining structure 24 primarily serves to fix the first dielectric waveguide 10 to the gantry support structure 18. This means that, as a result of the embodiment of the first dielectric waveguide 10, the electromagnetic fields, during the conveying of electromagnetic waves through the first dielectric waveguide 10, are concentrated above all on the conductor body 22 and only extend into the retaining structure 24 to a small degree.

Figure 2:
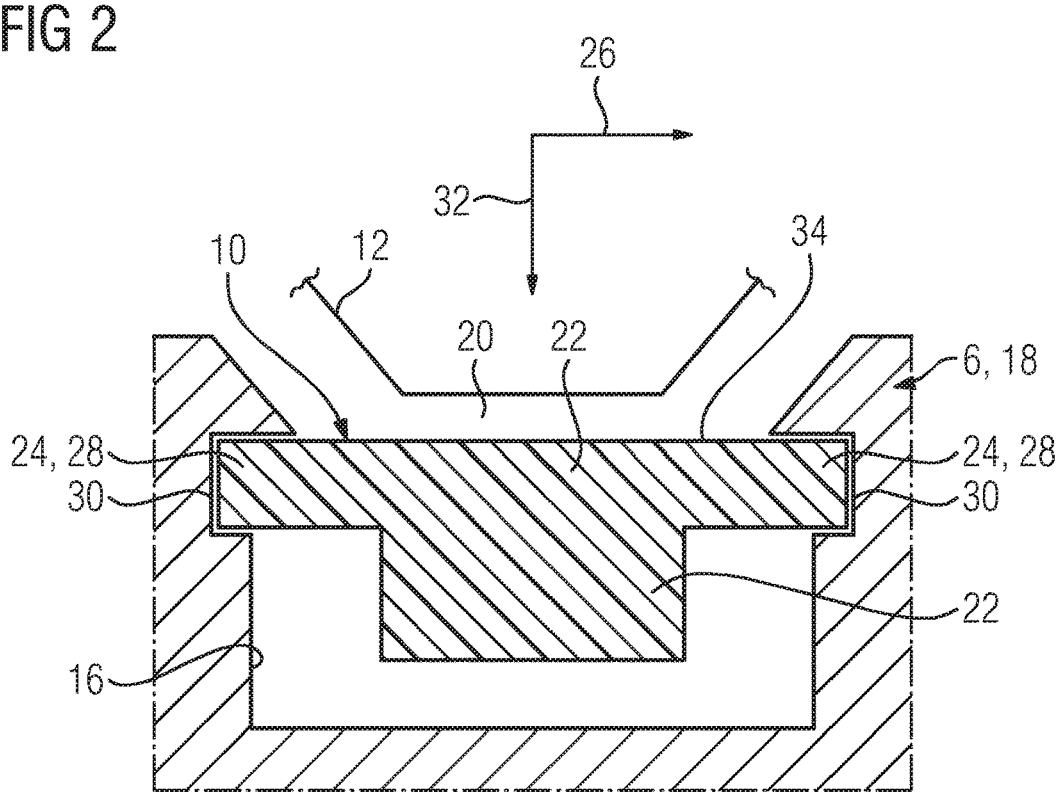
FIG. 2 shows, in a kind of cross-sectional diagram, the groove and the first dielectric waveguide inserted into the groove.

A possible version of a first dielectric waveguide 10 is shown in FIG. 2. Here the first dielectric waveguide 10, seen in cross-section, has a square-shaped conductor body 22, on which, on two opposing sides, seen in the transverse direction 26, it is adjoined by two retaining webs 28, which flank the conductor body 22 like two lateral wings and which, in this embodiment variant, form the retaining structure 24. In this case the conductor body 22 and the two retaining webs 28 then form a kind of T shape.

As can further be seen from FIG. 2, the first dielectric waveguide 10 in this example embodiment is arranged recessed in the groove 16 of the gantry support structure 18 and, when the plug connection is made, the two retaining webs 28 engage behind an undercut 30 in the groove 16, so that the first dielectric waveguide 10 will be held by a form fit in the groove 16.

The contact between the first dielectric waveguide 10 and the gantry support structure 18 in the area of the groove 16 is further reduced to a minimum, and this is done in the area of the outer ends of the retaining webs 28. In all other areas there is a free space around the first dielectric waveguide 10, in which air is typically present.

Figure 3:
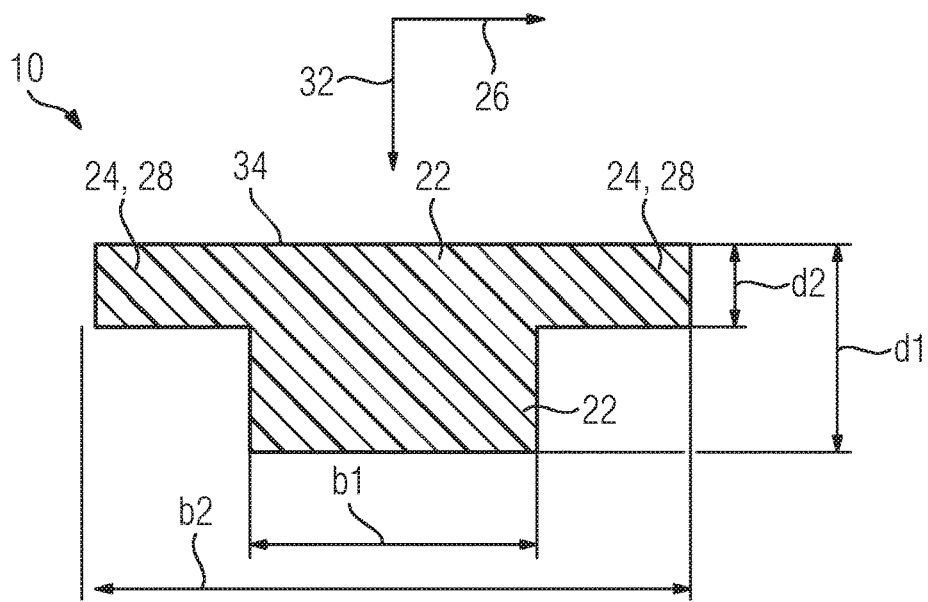
FIG. 3 shows, in a kind of cross-sectional diagram, the first dielectric waveguide.

Example dimensions of a first dielectric waveguide 10 for an imaging facility presented here are indicated in FIG. 3, wherein b2=10 mm, b1=4 mm, d1=2 mm and d2=1 mm.

Further embodiment variants of the first dielectric waveguide 10 are reproduced in FIG. 4 to FIG. 7, wherein said variants are distinguished from that described previously by a differing cross-section. Common to all embodiment variants is a square-shaped conductor body 22, which is adjoined on two opposing sides in each case by a retaining web 28.

Figure 4:
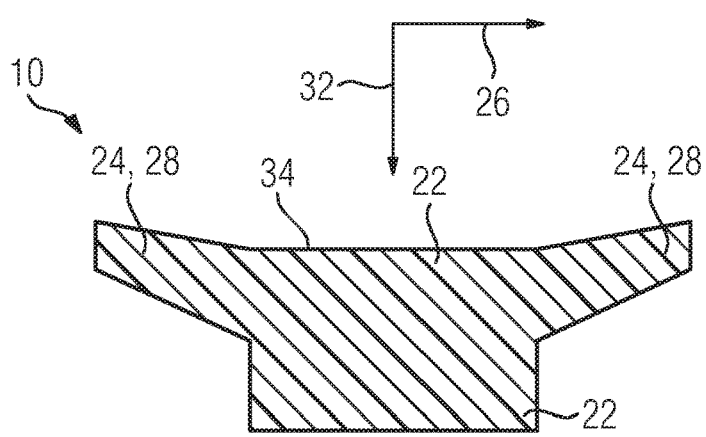
FIG. 4 shows, in a kind of cross-sectional diagram, a first alternate version of the first dielectric waveguide.
Figure 5:
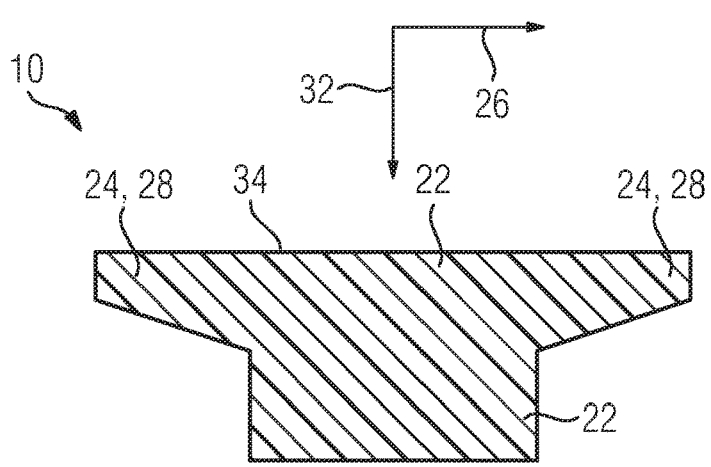
FIG. 5 shows, in a kind of cross-sectional diagram, a second alternate version of the first dielectric waveguide.

In FIG. 4 and FIG. 5 the retaining webs 28 taper in this variant in the transverse direction 26 and against the transverse direction 26, i.e. in a direction in each case that points away from the conductor body 22. In the case of the embodiment variant according to FIG. 4, the retaining webs 28 are also angled, and this is done against the plug-in direction 32 of the plug connection, into which the first dielectric waveguide 10 will be guided to make the plug connection.

Figure 6:
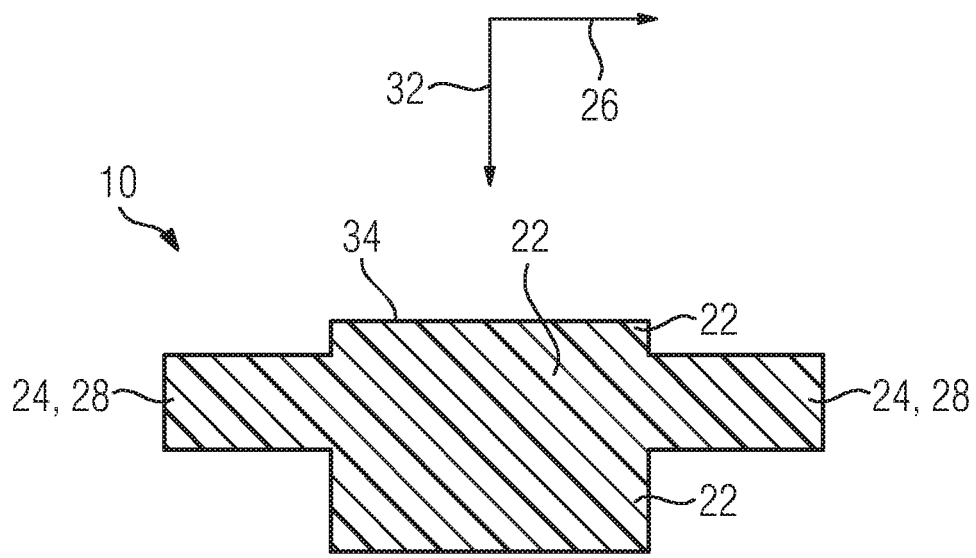
FIG. 6 shows, in a kind of cross-sectional diagram, a third alternate version of the first dielectric waveguide
Figure 7:
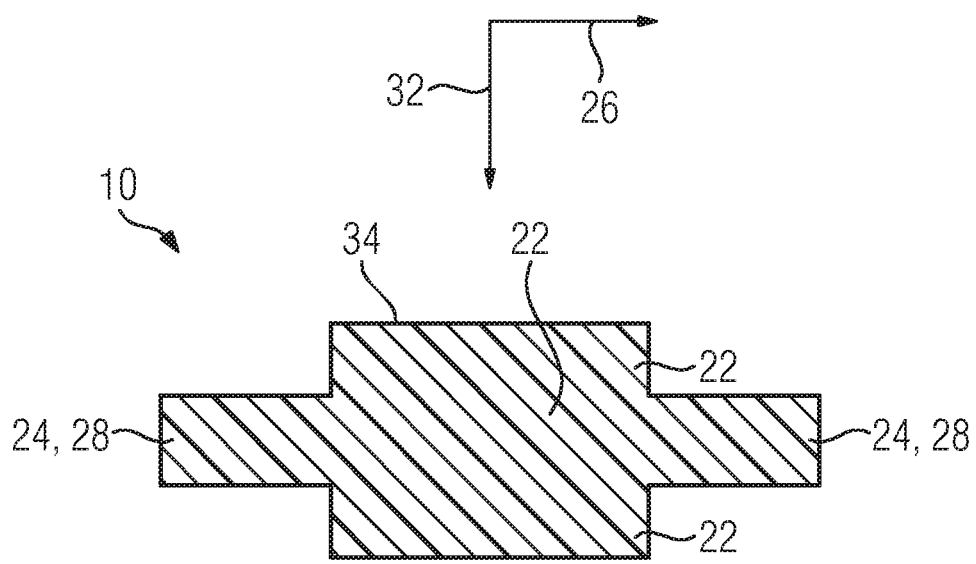
FIG. 7 shows, in a kind of cross-sectional diagram, a fourth alternate version of the first dielectric waveguide.

By contrast with the embodiment variants in accordance with FIG. 2 to FIG. 5, the retaining webs 28 in the two embodiment variants in accordance with FIG. 6 and FIG. 7 are not formed flush on the conductor body 22, but instead at a position offset in the plug-in direction 32, i.e. effectively somewhat below the upper side 34 of the conductor body 22, which faces towards the second dielectric waveguide 12 in the computed tomograph 2. These two embodiment variants are of particular advantage when the first dielectric waveguide 10 is not part of the rotatable gantry 6, but of the fixed base 4 and accordingly is attached to a support structure of the fixed base 4 via a plug connection. In this case no large forces, i.e. in particular no centrifugal forces, then occur during operation, which act against the plug connection, and accordingly this type of plug connection is then designed for lower forces, in particular forces acting against the plug-in direction 32.

The invention is not restricted to the example embodiment described above. Instead other variants of the invention can also be derived herefrom by the person skilled in the art, without departing from the subject matter of the invention. In particular all individual features described in conjunction with the example embodiment are also able to be combined in another way, without departing from the subject matter of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus, comprising:
a transmitter configured to transmit data; and
a receiver, the transmitter and the receiver being relatively movable with respect to another of the receiver and the transmitter; and
a coupler, the receiver being configured to receive data from the transmitter via the coupler even during a relative movement between transmitter and receiver, the coupler including a dielectric waveguide including a conductor body portion and a retaining structure portion, the conductor body portion being configured to fit within a guide of a gantry support structure of an imaging facility and the retaining structure portion being configured to fit into a groove in the gantry support structure of the imaging facility.

2. The apparatus of claim 1, wherein the conductor body portion and the retaining structure portion are made of a same material.

3. The apparatus of claim 1, wherein the retaining structure portion forms a first part of a plug connection.

4. The apparatus of claim 1, wherein the retaining structure portion is embodied by a plurality of retaining arms, formed on the conductor body portion.

5. The apparatus of claim 1, wherein the dielectric waveguide forms a profile strip.

6. The apparatus of claim 5, wherein the profile strip embodies the dielectric waveguide, viewed in cross-section, including a plurality of retaining webs extending transversely to a longitudinal extent of the profile strip.

7. The apparatus of claim 6, wherein, viewed in cross-section, a first retaining web, of the plurality of retaining webs, is formed directly on one side the conductor body portion and a second retaining web, of the plurality of retaining webs, is formed directly on another opposing side of the conductor body portion.

8. The apparatus of claim 6, wherein the plurality of retaining webs, viewed in cross-section, taper towards an outside of the conductor body portion.

9. The apparatus of claim 6, wherein the retaining structure portion forms a first part of a plug connection and wherein the plurality of retaining webs, viewed in cross-section, are angled against a plug-in direction of the plug connection.

10. The apparatus unit of claim 9, wherein the plurality of retaining webs, viewed in cross-section, include a flush joint to an upper side of the conductor body portion, a normal of the flush joint being directed against the plug-in direction of the plug connection.

11. The apparatus of claim 1, wherein the conductor body portion is embedded in the retaining structure portion.

12. An imaging facility, comprising the apparatus of claim 1.

13. The imaging facility of claim 12, wherein the transmitter is part of a rotatable gantry including the gantry support structure and wherein the receiver is part of a fixed base.

14. The imaging facility of claim 13, wherein at least the retaining structure portion of the dielectric waveguide is configured to fit into a groove in the gantry support structure.

15. The imaging facility of claim 14, wherein the groove in the gantry support structure forms a part of a plug connection with the dielectric waveguide.

16. The apparatus of claim 2, wherein the dielectric waveguide is embodied as a single structure including the conductor body portion and the retaining structure portion being integrally formed.

17. The apparatus of claim 2, wherein the retaining structure portion forms a first part of a plug connection.

18. The apparatus of claim 17, wherein the retaining structure portion is embodied by a plurality of retaining arms, formed on the conductor body.

19. The apparatus of claim 5, wherein the profile strip with an end-to-end uniform cross-section.

20. The apparatus of claim 6, wherein the profile strip embodies the first dielectric waveguide, viewed in cross-section, including a plurality of retaining webs extending transversely to a longitudinal extent of the profile strip and extending transversely to a plug-in direction of a plug connection.

21. The imaging facility of claim 13, wherein the dielectric waveguide forms the transmitter and is fixed to the gantry support structure.

22. The apparatus of claim 1, wherein the conductor body portion is embodied to convey electromagnetic waves within a frequency range of 40 to 300 GHz.

23. The imaging facility of claim 12, wherein at least the retaining structure portion of the dielectric waveguide is configured to fit into a groove in the gantry support structure.

24. The imaging facility of claim 23, wherein the conductor body portion of the dielectric waveguide is configured to sit within, but not contact, the gantry support structure.

25. The apparatus of claim 1, wherein the conductor body portion and the retaining structure portion are made of different materials.

26. The imaging facility of claim 13, wherein the conductor body portion is embodied to convey electromagnetic waves within a frequency range of 40 to 300 GHz.

27. An imaging facility, comprising:
a transmitter configured to transmit data, the transmitter being part of a rotatable gantry including a gantry support structure; and
a receiver, the receiver being part of a fixed base, and the transmitter and the receiver being relatively movable with respect to another of the receiver and the transmitter; and
a coupler, the receiver being configured to receive data from the transmitter via the coupler even during a relative movement between transmitter and receiver, the coupler including a dielectric waveguide including a conductor body portion and a retaining structure portion, at least the retaining structure portion of the dielectric waveguide being configured to fit into a groove in the gantry support structure.

28. The imaging facility of claim 27, wherein the conductor body portion of the dielectric waveguide is configured to sit within, but not contact, the gantry support structure.

29. The imaging facility of claim 27, wherein the conductor body portion and the retaining structure portion are made of a same material.

30. The imaging facility of claim 27, wherein the conductor body portion and the retaining structure portion are made of different materials.

31. The imaging facility of claim 27, wherein the retaining structure portion is embodied by a plurality of retaining arms, formed on the conductor body portion.

32. The imaging facility of claim 27, wherein the dielectric waveguide forms the transmitter and is fixed to the gantry support structure.

33. The imaging facility of claim 27, wherein the conductor body portion is embodied to convey electromagnetic waves within a frequency range of 40 to 300 GHz.

* * * * *